United States Patent [19]
Jagger et al.

[11] Patent Number: 4,676,783
[45] Date of Patent: Jun. 30, 1987

[54] RETRACTABLE SAFETY NEEDLE

[75] Inventors: Janine C. Jagger; Richard D. Pearson; Patrice G. Guyenet, all of Charlottesville, Va.

[73] Assignee: The University of Virginia Alumni Patents Foundation, Charlottesville, Va.

[21] Appl. No.: 771,640

[22] Filed: Sep. 3, 1985

[51] Int. Cl.$^4$ .............................................. A61M 5/00
[52] U.S. Cl. .................................. 604/171; 604/177; 604/198; 604/162
[58] Field of Search ............... 604/171, 177, 198, 263, 604/162

[56] References Cited

U.S. PATENT DOCUMENTS

| | | | |
|---|---|---|---|
| 3,055,361 | 9/1962 | Ballard | 604/162 |
| 3,536,073 | 10/1970 | Farb | 604/162 |
| 3,572,334 | 3/1971 | Petterson | 604/162 |
| 3,670,727 | 6/1972 | Reiterman | 604/177 |
| 3,910,272 | 10/1975 | Forberg | 604/162 |
| 4,160,450 | 7/1979 | Doherty | 604/162 |
| 4,425,120 | 1/1984 | Sampson et al. | 604/198 |

Primary Examiner—C. Fred Rosenbaum
Assistant Examiner—Sherri E. Vinyard
Attorney, Agent, or Firm—James C. Wray

[57] ABSTRACT

An intravenous needle with a sharpened distal end has a proximal end fixed within a first enlarged end of an inner tube. The enlarged end of the inner tube is held tightly within a first end of an outer tube by friction. The needle passes through a constricted opening in the first end of the outer tube. The second end of the inner tube passes through a constricted opening in the second end of the outer tube. The needle is used by gripping soft plastic wings on the outer tube and removing a needle cover from a nipple on the first end of the outer tube. The needle is then inserted in the desired location and the outer tube and a protruding end of the inner tube are taped in place. Fluids are permitted to flow through the inner tube and needle. When use is complete, the needle is removed from the vein, the protruding end of the inner tube is pulled outward, pulling the first end of the inner tube and the needle into the outer tube. The first end of the inner tube tightly wedges within the second end of the outer tube, holding the needle totally within the outer tube. Finally, the retracted used needle assembly is discarded, encased in the outer tube.

9 Claims, 3 Drawing Figures

RETRACTABLE SAFETY NEEDLE

BACKGROUND OF THE INVENTION

Needlestick injuries are intended to be avoided by properly disposing of needles.

Usually used needles are recapped with the same cover that originally covered the needles before use or by similar covers or tubes before a needle is discarded. That method requires movement of hands toward needles and may promote needlestick injuries during the recapping.

Often needles are disposed of by tossing them into nearby refuse containers, creating danger to those who handle the refuse containers. Usually contaminated needles are placed on trays for carrying to a disposal facility which may be distant from the place where the needles are used. That creates danger en route to persons carrying the trays or pushing carts on which the trays are located or to close by persons who may be injured when the tray slips or spills.

Needle destruction devices are available, but the destructive devices may not be convenient and may be placed permanently at a position that requires the movement of contaminated needles to the destruction devices.

Problems remain in the prevention of needlestick injuries caused by non compliance with established procedures or by inherently unsafe features of the established procedures.

The present invention overcomes problems associated with the prior art.

SUMMARY OF THE INVENTION

An intravenous needle with a sharpened distal end has a proximal end fixed within a first enlarged end of an inner tube. The elarged end of the inner tube is held tightly within a first end of an outer tube by friction. The needle passes through a constricted opening in the first end of the outer tube. The second end of the inner tube passes through a constricted opening in the second end of the outer tube. The needle is used by gripping soft plastic wings on the outer tube and removing a needle cover from a nipple on the first end of the outer tube. The needle is then inserted in the desired location and the outer tube and a protruding end of the inner tube are taped in place. Fluids are permitted to flow through the inner tube and needle. When use is complete, the needle is removed from the vein, the protruding end of the inner tube is pulled outward, pulling the first end of the inner tube and the needle into the outer tube. The first end of the inner tube tightly wedges within the second end of the outer tube, holding the needle totally within the outer tube. Finally, the retracted used needle assembly is discarded, encased in the outer tube.

An intravenous administration system has a retractable safety needle. A steel needle intravenous administration device provides a way to safely resheath contaminated intravenous needles to reduce the risk of accidental needlestick injuries to health care personnel. The device uses a steel needle bonded to standard clear plastic tubing to form a closed system. The needle/tubing assembly is encased in, but is not bonded to, a closely fitting plastic cylinder slightly longer than the length of the needle. The needle protrudes from one end of the cylinder. The cylinder has two small wings at the sides for easy manipulation of the needle. A plastic tab is bonded to the tubing at a position spaced from the cylinder. After the intravenous device is removed from the patient, the contaminated needle is retracted into the plastic cylinder by grasping the wing and pulling axially on the tab. The cylinder grips the plastic tubing by friction which is sufficient to keep the needle from withdrawing during insertion of the device. The grip is overcome, allowing the needle to be pulled into the cylinder, when appropriate force is applied. The needle is prevented from being pulled too far through the cylinder by a constriction at the second end of the cylinder and is prevented from moving out of the first end of the cylinder by friction. The cylinder serves as a protective barrier, protecting hospital personnel from hazardous contaminated needles.

A disposable medical needle apparatus comprises an outer tube and an inner tube mounted in a concentric friction fit relationship. An intravenous needle has a sharpened distal end and a proximal end. The proximal end of the needle is tightly gripped within a first end of the inner tube, and the needle extends outward therefrom through a first constricted opening in a first end of the outer tube. A second end of the inner tube extends outward through a second constriction in the second end of the outer tube. First gripping means on the outer tube provides for gripping the outer tube and second gripping means on the second end of the inner tube provides for gripping the inner tube when sliding the inner tube and needle axially in the outer tube. Connection means on the second end of the inner tube connects the inner tube to a fluid supply.

Preferably, the second constriction in the second end of the outer tube comprises wedge shaped means opening toward the first end of the outer tube for clamping the first end of the inner tube when the second gripping means is pulled in an axial direction away from the outer tube.

In a preferred embodiment, the first end of the inner tube comprises an enlarged head for tightly gripping an inner wall of the outer tube and for preventing outward passage of the first end of the inner tube beyond the second constriction at the second end of the outer tube when the second gripping means pulls the inner tube axially in the outer tube.

Preferably, the first gripping means comprises a soft plastic wing extending outward from the outer tube, and the second gripping means comprises a plastic tab extending outwardly from the second end of the inner tube.

Preferably, the first gripping means comprises soft plastic wings extending oppositely from the outer tube, and the second gripping means comprises plastic tabs extending oppositely from the second end of the inner tube.

In a preferred embodiment, a nipple extends axially on the first end of the outer tube and a tubular plastic cover connected to the nipple extends axially therefrom over the needle and beyond the sharpened distal end of the needle for covering the needle prior to use.

A preferred method of using intravenous needles comprises holding an inner tube fixed within an outer tube, extending a needle from a proximal end fixed within a first end of the inner tube through a constricted opening in a first end of the outer tube, gripping the outer tube and pushing a sharpened distal end of the needle into the desired position, flowing fluids through the inner tube and the needle, discontinuing the flow of fluids through the inner tube and the needle, removing the needle from the vein, protruding a second end of the inner tube through a constricted opening in the second end of the outer tube, gripping the second end of the inner tube and pulling the first end of the inner tube and the needle axially within the outer tube, tightly engaging the first end of the inner tube with the second end of the outer tube and holding the needle within the outer tube.

These and other objects and features of the invention are apparent in the disclosure which includes the above and ongoing specifications with the claims and the drawings.

DETAILED DESCRIPTION OF THE DRAWINGS

Figure 1:
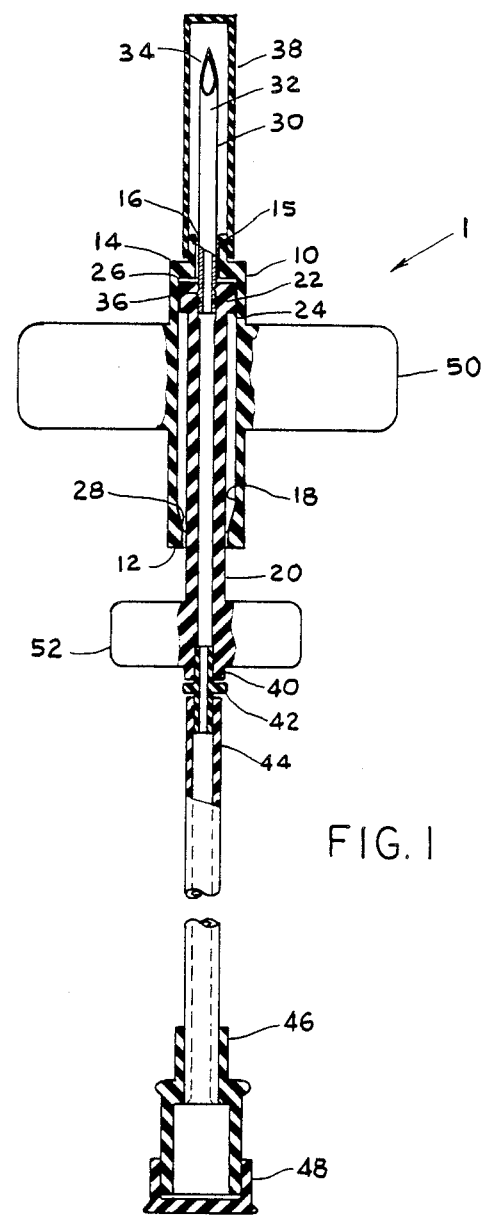
FIG. 1 is a elevational view partly in section of the intravenous needle assembly of the present invention.

Referring to FIG. 1 a needle assembly of the present invention is generally indicated by the numeral 1. A cylinder 10 has two ends 12 and 14 with restricted openings. The first end 14 has a projecting nipple 15 with a constriction 16 in a form of a restricted axial opening. The inner cavity 18 of the cylinder 10 slidingly receives inner tube 20 while gripping the enlarged first end 22 of the inner tube. The outer surface 24 of the enlarged end 22 is tighly gripped by the inner surface 26 at the first end of cavity 18 to hold the unused needle in a protruded usable condition. The second end of the cavity 18 is in a form of a wedge-shaped constriction 28 which tightly grips the outer surface 24 of the enlarged end 22 of tube 20 when tube 20 is pulled rearward or downward as shown in FIG. 1. The gripping of the enlarged end 22 within the wedge 28 holds the needle 30 entirely within the outer tube 10 preventing accidental contact with the needle 30, its shaft 32, or its sharpened distal end 34. The proximal end 36 of the needle is tightly gripped within the first end 22 of the inner tube 20. A protector tube 38 is held on the nipple 15 to prevent accidental contact with the protruded needle 30 before the needle is used.

The second end 40 of the inner tube 20 is provided with a connector 42 for connection to an elongated flexible connector tube 44 which is provided on its distal end with a connector 46 for connecting tube 44 to a supply tube connected to a fluid container. Cap 48 protects the connector 46 before it is used.

Figure 2:
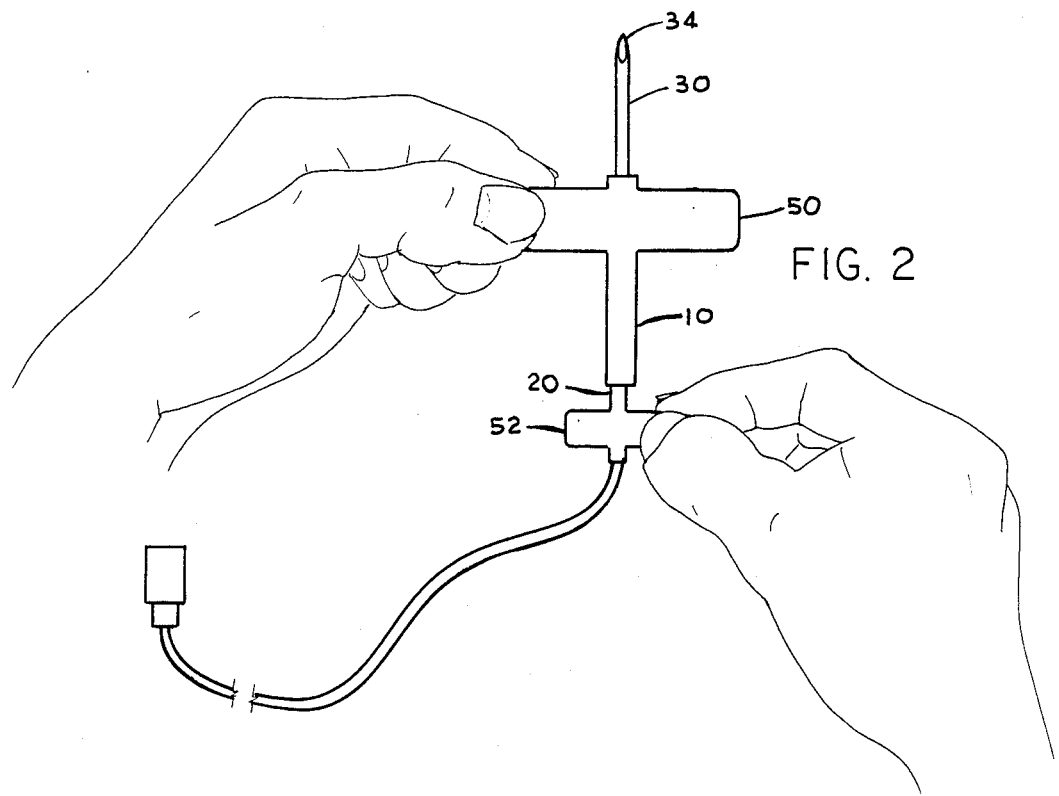
FIG. 2 is a view showing the gripping of the elements for retracting the needle.
Figure 3:
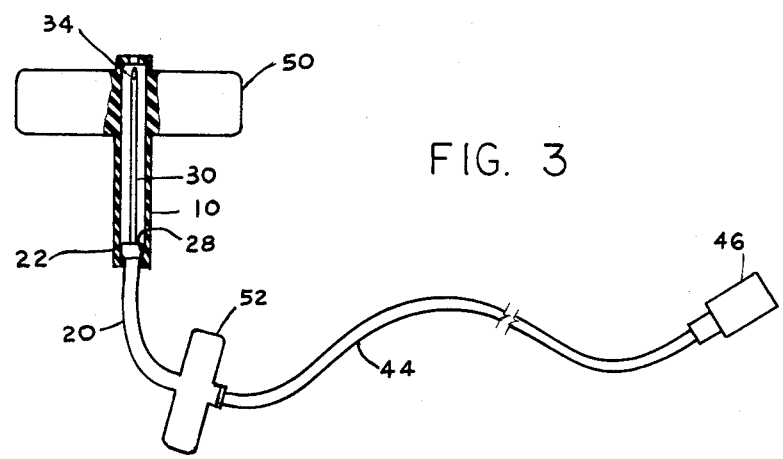
FIG. 3 is a view partially cut away showing the retracted needle in the protective cylinder.

In use, one grips wings 50 and then removes the tubular cover 38 from the nipple 16. Gripping the wings 50, one slides the needle into its desired position. After the needle has been used, wings 50 and tabs 52 are gripped separately as shown in FIG. 2, and tabs 52 and tube 20 are pulled in an axial direction away from wings 50, extending tube 20 from outer tube 10 and pulling needle 30 and sharpened distal end 34 into the outer tube as shown in FIG. 3. The enlarged first end 22 of the inner tube 20 is firmly gripped by the inner wedge surface 28, preventing further relative movement between needle 30 and the outer protective tube 10, as shown in FIG. 3.

While the invention has been described with reference to specific embodiments, modifications and variations may be constructed without departing from the scope of the invention.

The scope of the invention is defined in the following claims.

We claim:

1. Disposable medical needle and apparatus for preventing accidental needle-stick injuries comprising,
    an outer tube having opposite first and second ends with constricted openings formed in each of the outer tube ends
    an inner tube mounted in a concentric friction fit relationship with the outer tube and having opposite first and second ends with openings formed in each of the inner tube ends,
    an intravenous needle having a sharpened distal end and a proximal end, the proximal end of the needle being tightly gripped within the opening of the first end of the inner tube, and the needle extending outward therefrom through the constricted opening of the first end of the outer tube, the second end of the inner tube extending ouward through the opening of the second end of the outer tube, and
    first gripping means on the outer tube and second gripping means on the second end of the inner tube, the first and second gripping means for imparting relative axial movement between the inner and outer tubes in opposite directions to withdraw the needle into the outer tube,
    wherein the outer tube does not act as a fluid conduit.

2. The apparatus of claim 1 wherein the second constriction in the second end of the outer tube comprises wedge shaped means opening toward the first end of the outer tube for clamping the first end of the inner tube when the second gripping means is pulled in an axial direction away from the outer tube.

3. The apparatus of claim 1 wherein the first end of the inner tube comprises an enlarged head for tightly gripping an inner wall of the outer tube and for preventing outward passage of the first end of the inner tube beyond the second constricted opening at the second end of the outer tube when the second gripping means pulls the needle axially in the outer tube.

4. The apparatus of claim 1 wherein the first gripping means comprises a soft plastic wing extending outward from the outer tube and wherein the second gripping means comprises a plastic tab extending outwardly from the second end of the inner tube.

5. The apparatus of claim 1 wherein the first gripping means comprises soft plastic wings extending oppositely from the outer tube and wherein the second gripping means comprises plastic tabs extending oppositely from the second end of the inner tube.

6. The apparatus of claim 1 further comprising a nipple extending axially on the first end of the outer tube and a tubular plastic cover connected to the nipple and extending axially therefrom over the needle and beyond the sharpened distal end of the needle for covering the needle prior to use.

7. The method of using intravenous needles comprising holding an inner tube fixed within an outer tube, extending a needle from a proximal end fixed within a first end of the inner tube through a constricted opening in a first end of the outer tube, gripping the outer tube and pushing the needle into the desired position into a vein, flowing fluids through the inner tube and the needle, discontinuing the flow of fluids through the inner tube and the needle, removing the needle from the vein, protruding a second end of the inner tube through a constricted opening in the second end of the outer tube, gripping the second end of the inner tube and pulling the first end of the inner tube and the needle axially within the outer tube, tightly engaging the first end of the inner tube with the second end of the outer tube and holding the needle within the outer tube, wherein the outer tube does not act as a fluid conduit.

8. The apparatus of claim 2 further comprising means on an inner surface of the outer tube for tightly engaging the first end of the inner tube and holding the needle within the outer tube after the inner tube is slid within the outer tube.

9. The apparatus of claim 1 further comprising connection means on the second end of the inner tube for connecting the inner tube to a fluid supply.

* * * * *